United States Patent [19]

Mitsche et al.

[11] 4,098,874

[45] Jul. 4, 1978

[54] METHOD OF PREPARATION OF ALUMINA CATALYST SUPPORT OR CARRIER MATERIAL

[75] Inventors: Roy T. Mitsche, Wauconda; George N. Pope, Mc Henry, both of Ill.

[73] Assignee: UOP Inc., Des Plaines, Ill.

[21] Appl. No.: 788,376

[22] Filed: Apr. 18, 1977

[51] Int. Cl.$^2$ .......................... C01F 7/02; B01J 21/04
[52] U.S. Cl. .................................. 423/628; 252/463; 252/466 R; 423/631; 423/630
[58] Field of Search ............... 423/628, 625, 630, 631; 252/463

[56] References Cited

U.S. PATENT DOCUMENTS

| | | | |
|---|---|---|---|
| 2,809,170 | 10/1957 | Cornelius et al. | 423/628 |
| 3,353,910 | 11/1967 | Cornelius et al. | 423/628 |
| 3,852,190 | 12/1974 | Buss et al. | 423/628 |
| 3,894,963 | 7/1975 | Gerdes et al. | 423/628 |
| 3,975,510 | 8/1976 | Leach et al. | 423/628 |
| 4,003,851 | 1/1977 | Ebel et al. | 252/463 |
| 4,045,372 | 8/1977 | Warthen et al. | 252/463 |

*Primary Examiner*—Herbert T. Carter
*Attorney, Agent, or Firm*—James R. Hoatson, Jr.; Robert W. Welch; William H. Page, II

[57] ABSTRACT

An alumina composition particularly useful as a catalyst support or carrier material is disclosed. The alumina is characterized by a method of preparation which comprises admixing an alpha-alumina monohydrate with an alkaline solution having a pH of at least about 7.5 and forming a stable suspension. A salt of a strong acid is commingled with the suspension to form a paste or dough which is subsequently formed into extrudates, and dried and calcined.

9 Claims, No Drawings

METHOD OF PREPARATION OF ALUMINA CATALYST SUPPORT OR CARRIER MATERIAL

Alumina is extensively employed in the chemical and petroleum industries as an adsorbent, a catalyst, and as a support or carrier for other catalytic materials. In particular, activated alumina has been widely accepted in the petroleum industry as a catalyst, or more frequently as a catalyst support or carrier material, to effect the various hydrocarbon conversion processes generally associated with petroleum refining, and the adsorbent characteristics of activated alumina make it especially useful for the selective removal of impurities from a process stream.

One of the more useful and far less costly methods of preparing the alumina in an acceptable particulate form comprises extruding the alumina in the form of a paste or dough — an alpha-alumina monohydrate being particularly adapted to the extrusion process. In the more conventional extrusion methods, it is the practice to admix a finely divided form of the alumina with a peptizing agent and sufficient water to form a paste or dough of extrudable consistency. It has been observed that the wet powdered form of the alumina is easily extruded provided that little if any work has been exerted on it. However, a uniform paste or dough so essential to product strength and product reproducibility is not as readily achieved. It is contemplated that this is largely the result of the mixture's tendency to set to a paste or dough before the peptizing agent becomes uniformly distributed in the mixture, and the further result of the thixotropic nature of the dough or paste and its tendency toward localized sol formation under conditions of intense mixing.

It is therefore an object of this invention to present a novel method of preparing reproducible, uniform alumina extrudate particles, and an improved alumina extrudate product suitable for use as an adsorbent, a catalyst, or a catalyst support or carrier material.

In one of its broad aspects, the present invention embodies an alumina composition characterized by a method of preparation which comprises admixing a finely divided alpha-alumina monohydrate with an aqueous alkaline solution having a pH of at least about 7.5 and forming a stable suspension; commingling a metal salt of a strong acid, or an aqueous solution thereof, with said suspension and converting the suspension to a paste or dough; extruding the paste or dough; and drying and calcining the extruded alumina product.

One of the more specific embodiments relates to an alumina composition characterized by a method of preparation which comprises admixing a finely divided alumina with an aqueous ammoniacal solution having a pH of from about 7.5 to about 8.5 and forming a stable suspension, said alumina being a water hydrolysis product of an aluminum alkoxide; commingling a metal nitrate salt, or an aqueous solution thereof, with said suspension and converting the suspension to a paste or dough; extruding the paste or dough; and drying and calcining the extruded alumina product at a temperature of from about 450° to about 850° C.

A still more specific embodiment concerns an alumina composition characterized by a method of preparation which comprises admixing a finely divided alumina with an aqueous ammoniacal solution having a pH of from about 7.5 to about 8.5 and forming a stable suspension, said alumina being a water hydrolysis product of an aluminum alkoxide produced by the Ziegler process; commingling sufficient aluminum nitrate, or an aqueous solution thereof, with said suspension to provide from about 2 to about 10 wt. % of the alumina product and converting the suspension to a paste or dough; extruding the paste or dough; and drying and calcining the extruded alumina product at a temperature of from about 550° to about 750° C. to provide a surface area of from about 165 to about 215 $m^2/g$ and a pore volume of from about 0.3 to about 0.4 cc/g in the pore diameter range of from about 20 to about 80 Angstroms.

Other objects and embodiments of the present invention will become apparent in the following more detailed specification.

The alpha-alumina monohydrate employed herein is preferably an alpha-alumina monohydrate derived from the water hydrolysis of an aluminum alkoxide. More preferably, the alpha-alumina monohydrate is a product of the well-known Ziegler process. The alpha-alumina monohydrate is thus preferably prepared stepwise starting with the reaction of aluminum, hydrogen and ethylene. After a further polymerization step with ethylene, the trialkyl aluminum polymerization product is oxidized to form an aluminum alkoxide which, on subsequent water hydrolysis, yields an alumina slurry and an alcohol product. The alumina recovered from the reaction mixture is generally treated for the removal of residual alcohols, for example by solvent extraction, and/or steam stripping, and then dried to produce the alpha-alumina monohydrate in a finely divided state.

Pursuant to the present invention, the finely divided alpha-alumina monohydrate is admixed with an aqueous alkaline solution having a pH of at least about 7.5, and preferably from about 7.5 to about 8.5. The alpha-alumina monohydrate added to the stirred aqueous alkaline solution forms a stable suspension having the consistency of a light whipped cream — the suspension being Newtonian in character with little if any thixotropic or dilatant behavior.

The alumina is preferably admixed with sufficient of aqueous solution to provide an extrudable paste or dough comprising from about 30 to about 60 wt. % alumina. The aqueous alkaline solution is preferably an aqueous ammoniacal solution. Suitable ammoniacal solutions include solutions of bases such as ammonium hydroxide, hydroxylamine, hydrazine, tetramethylammonium hydroxide, etc., or a strong organic amine like methylamine, dimethylamine, ethylamine, diethylamine, propylamine, diisopropylamine, n-butylamine, t-butylamine, diisobutylamine, n-amylamine, n-hexylamine, ethylenediamine, hexamethylenediamine, benzylamine, aniline, piperizine, piperadine, and the like, the selected base being employed in sufficient concentration to provide a pH of at least about 7.5, and preferably from about 7.5 to about 8.5.

With the addition of a metal salt of a strong acid to the stirred suspension as herein contemplated, the suspension becomes very fluid for a brief period permitting the suspension to become thoroughly and uniformly mixed before setting to a firm extrudable paste. The selected metal salt is conveniently an aluminum salt whereby the aluminum provides a portion of the alumina of the finished product. However, the metal salt may comprise one or more metals exhibiting a catalytic effect with respect to one or more hydrocarbon conversion reactions whereby said metal or metals appear as a catalytic component of the final alumina product. The metal salt is suitably added to the stirred suspension as an aqueous solution thereof in an amount to provide sufficient acid anions to convert said suspension to an extrudable paste, an amount which is usually equivalent to that required to provide from about 1 to about 10 wt. % of the metal content of the finished product. Suitable metal salts of a strong acid particularly include the nitrates, sulfates and halides, and especially the nitrates, for example, aluminum nitrate, ferric nitrate, nickel nitrate, cobalt nitrate, chromium nitrate, copper nitrate, palladium nitrate, silver nitrate, zinc nitrate, stannous and stannic nitrate and the like.

Extrusion of the paste or dough can be effected in accordance with prior art practice. Thus, utilizing a conventional screw type extruder, the dough or paste is processed through a die plate generally comprising orifice openings in the 1/32-¼ inch diameter range. The freshly extruded material may be collected in the form of strands of indefinite or random lengths to be dried and subsequently broken into extrudate particles; or the freshly extruded material may be cut into random or predetermined lengths and subsequently dried; or the freshly extruded material may be formed into spheres, for example, by the process whereby the extrudate strands are collected in a spinning drum — the strands becoming segmented and spheroidized under the spinning influence of the drum.

In any case, the extrudate is dried and subsequently calcined. Suitable drying is accomplished at a temperature of from about 100° to about 120° C. in an air atmosphere using a forced draft oven. The extrudate product can be dried and calcined at a temperature of from about 450° to about 850°, but preferably at a temperature of from about 550° to about 750° C. in a flow of air containing 1 to 5 wt. % steam to produce a calcined product having a surface area of from about 165 to about 215 m$^2$/g and a pore volume of from about 0.3 to about 0.4 cc/g and the pore diameter range of from about 20 to about 80 Angstroms.

The alumina composition of this invention is advantageously employed as a support or carrier material for other catalytic components to promote various hydrocarbon conversion reactions including dehydrogenation of specific hydrocarbons or petroleum fractions, isomerization of specific hydrocarbons or petroleum fractions, hydrocracking of lower molecular weight hydrocarbons such as occur in the kerosene and gas oil boiling range, and the oxidation of hydrocarbons to provide first, second and third stage oxidation products. Reaction conditions employed in the various hydrocarbon conversion reaction are those heretofore practiced. For example, alkylaromatic isomerization reaction conditions include a temperature of from about 0° to about 535° C., a pressure of from about atmospheric to about 1500 psig., a hydrogen to hydrocarbon mole ratio of from about 0.5 to about 20, and a liquid hourly space velocity of from about 0.5 to about 20. Likewise, a typical hydrocracking operation is effected at a pressure of from about 500 to about 1500 psig., a temperature of from about 200° to about 500° C., a liquid hourly space velocity of from about 4 to about 10, and a hydrogen circulation rate of from about 1000 to about 10,000 standard cubic feet per barrel of hydrocarbon charge (SCF/BBl).

The alumina composition of this invention is of particular advantage as a support or carrier material for a platinum group metal component, alone or in combination with a tin component, a rhenium component, a germanium component and/or a cobalt component to yield an improved reforming catalyst. The platinum group metal component is suitably composited with the support or carrier material by impregnation and/or ion-exchange techniques familiar to the art. For example, a soluble platinum group compound, that is, a soluble compound of platinum, palladium, rhodium, ruthenium, osmium and/or iridium, is prepared in aqueous solution, and the alumina particles soaked, dipped, or otherwise immersed therein. Suitable platinum group compounds include platinum chloride, chloroplatinic acid, ammonium chloroplatinate, dinitrodiamioplatinum, palladium chloride, and the like. It is common practice to impregnate the support carrier material with an aqueous chloroplatinic acid solution acidified with hydrochloric acid to facilitate an even distribution of platinum on the support or carrier material. The support or carrier material is preferably maintained in contact with the impregnating solution at ambient temperature conditions, suitably for at least about 30 minutes, and the impregnating solution thereafter evaporated to dryness. For example, a volume of the particulate support or carrier material is immersed in a substantially equal volume of impregnating solution in a steam jacketed rotary dryer and tumbled therein for a brief period at about room temperature. Steam is thereafter applied to the dryer jacket to expedite evaporation of the impregnating solution and recovery of substantially dry impregnated particles. Thus, a further embodiment of this invention relates to an alumina support or carrier material characterized by a surface area of from about 165 to about 215 m$^2$/g and a pore volume of from about 0.3 to about 0.4 cc/g in the pore diameter range of from about 20 to about 80 Angstroms, said alumina being impregnated with from about 0.1 to about 2.0 wt. % platinum.

As heretofore stated, the alumina composition of this invention is useful as a support or carrier material for a platinum group metal component alone or in combination with a tin component, a rhenium component, a germanium component and/or a cobalt component. The tin, rhenium, germanium and/or cobalt components may be composited with the support or carrier material in any conventional or otherwise convenient manner. Suitable methods include impregnation and/or ion-exchange of the support or carrier material with a suitable compound of one or more of said components in any desired sequence, with or without intermediate calcination. In the impregnation of the support or carrier material, it is a preferred practice to impregnate one or more of said components on said support or carrier material simultaneously with the platinum group metal component from a common impregnating solution. For example, when the added component is tin, stannic chloride is conveniently and advantageously prepared in common solution with chloroplatinic acid, the concentration of each component therein being sufficient to yield a catalyst product containing from about 0.01 to about 2.0 wt. % platinum and from about 0.1 to about 5.0 wt. % tin calculated as the elemental metal. Similarly, when the desired added component is rhenium, perrhenic acid and chloroplatinic acid can be prepared in a common aqueous solution to impregnate the support or carrier material, suitably with from about 0.01 to about 2.0 wt. % platinum and from about 0.01 to about 2.0 wt. % rhenium. Thus, another embodiment of this invention concerns an alumina support or carrier material characterized by a surface area of from about 165 to about 215 m$^2$/g and a pore volume of from about 0.3 to about 0.4 cc/g in the pore diameter range of from about 20 to about 80 Angstroms, said alumina being impregnated with from about 0.01 to about 2.0 wt. % platinum and from about 0.01 to about 2.0 wt. % rhenium.

The tin, rhenium, germanium and/or cobalt components and particularly the tin, germanium and cobalt components are advantageously composited with the alumina by including a suitable acid salt thereof in the aforementioned suspension prepared by admixing a finely divided alpha-alumina monohydrate with an aqueous alkaline solution. For example, an acid salt of tin such as stannous or stannic chloride, may be admixed with said suspension and serve not only as a precursor of the desired tin component, but also as the metal salt of a strong acid as herein contemplated. Following the extrusion process and subsequent calcination, the alumina is obtained comprising the tin component in intimate combination therewith and suitable for further impregnation and/or ion-exchange to incorporate, for example, the platinum group metal component.

The final catalyst composite generally will be dried at a temperature of from about 95° to about 315° C. for a period of from about 2 to about 24 hours or more, and finally calcined at a temperature of from about 375° to about 595° C. in an air atmosphere for a period of from about 0.5 to about 10 hours in order to convert the catalytic component substantially to the oxide form. Although not essential, it is preferred that the resultant calcined catalytic composite be subjected to a substantially water-free reduction step prior to its use in the conversion of hydrocarbons. This step is designed to insure a uniform and finely divided dispersion of the catalytic component throughout the carrier material. Preferably, substantially dry hydrogen is used as the reducing agent in this step. The reducing agent is contacted with the calcined catalyst at a temperature of from about 425° to about 650° C. and for a period of from about 0.5 to about 10 hours. This reduction treatment may be performed in situ as part of a start-up sequence if precautions are taken to predry the plant to a substantially water-free state and if substantially water-free hydrogen is used.

The reforming of gasoline boiling range petroleum fractions to improve the octane rating thereof is a process well known to the petroleum refining industry. The petroleum fraction may be a full boiling range gasoline fraction boiling in the 10°-220° C. range, although it is more often what is called a naphtha fraction, a gasoline fraction having an initial boiling point of from about 65° to about 120° C. and an end boiling point of from about 175° to about 220° C. Reforming conditions generally include a pressure of from about 50 to about 1000 psig and a temperature of from about 425° to about 595° C. The catalyst of this invention permits a stable reforming operation to be effected in a preferred pressure range of from about 50 to about 350 psig. utilizing a hydrogen/hydrocarbon mole ratio of from about 0.5 to about 10 and a liquid hourly space velocity of from about 0.5 to about 10. Preferably, a temperature of from about 485° to about 565° C., is employed.

The following examples are presented in illustration of certain preferred embodiments of this invention, and in illustration of the improved alumina catalyst support or carrier material derived from the practice of this invention. The examples are not intended as an undue limitation on the generally broad scope of the invention as set out in the appended claims.

EXAMPLE I

In this example, representative of one preferred embodiment of this invention, 4000 grams of a finely divided alpha-alumina monohydrate (Catapal SB alumina) was added to a rapidly stirred aqueous alkaline solution having a pH of about 7.5. The alumina contained about 25 wt. % volatile matter, and the alkaline solution consisted of 12.9 cc of concentrated ammonium hydroxide diluted to 3450 cc with water. The resulting slurry was a stable suspension having a light creamy consistency. The suspension was Newtonian in character and gave no indication of thixotropic or dilatant behavior. After about 30 minutes of continuous stirring, an aluminum nitrate solution was added, the solution consisting of 595 grams of $Al(NO_3)_3 \cdot 9H_2O$ dissolved in 1400 cc of water. The stirred suspension became very thin and extremely fluid for about 10 seconds and thereafter set to a thick paste with a solids content of about 33 wt. %. The paste was subsequently extruded, oven dried for about 12 hours at 110° C., and calcined for about 2 hours at 650° C. in air containing about 3 wt. % steam. The dried and calcined alumina product had a surface area of 217 m²/g, and a pore volume of about 0.35 cc/g in the 40-60 Angstrom diameter range.

About 250 cc of the alumina particles were immersed in 250 cc of an impregnating solution. The impregnating solution was prepared by admixing 46.9 cc of chloroplatinic acid (10 milligrams of platinum per cc), 9.5 cc of an ethanolic germanium tetrachloride solution (33 milligrams of germanium per cc), and 21.3 cc of concentrated hydrochloric acid, the solution being diluted to 250 cc with water. The alumina particles were tumbled in the solution for about ½ hour at room temperature utilizing a steam jacketed rotary dryer. Steam was thereafter applied to the dryer jacket and the solution evaporated to dryness in contact with the tumbling particles. The particles were subsequently calcined in air for ½ hour at 390° F., and for an additional ½ hour at 975° F. The calcined particles were thereafter reduced in hydrogen for about 1 hour at 1050° F. to yield a catalyst comprising 0.22 wt. % platinum, 0.15 wt. % germanium and about 1.0 wt. % chloride. The average bulk density was approximately 0.84 grams per cc.

The catalyst thus prepared was evaluated in a laboratory scale reforming plant comprising a reactor, a hydrogen separator and a debutanizer column. A hydrogen-rich recycle stream and the hydrocarbon charge were commingled and preheated to a desired temperature, the hydrocarbon charge stock being a naphtha fraction characterized by an API gravity at 15.5° C. of 66.4 and F-1 clear octane rating of 40, and an 85°-182° C. boiling range. The hydrogen-hydrocarbon mixture was passed downflow through a fixed catalyst bed contained in the reactor. The reactor effluent was passed through a high pressure-low temperature separator wherein a hydrogen-rich gaseous phase was separated from the liquid phase at a pressure of about 300 psig and a temperature of about 13° C. A portion of the gaseous phase was continuously recycled to the reactor to a high surface area sodium scrubber, and the excess over that required to maintain plant pressure was recovered as excess separator gas. The liquid phase was continuously withdrawn from the separator and passed to the debutanizer column where light ends were taken overhead as a debutanizer gas, and a $C_5+$ reformate product recovered as bottom.

The catalyst was evaluated over 10 test periods, each comprising a 12 hour line-out followed by a 12 hour test period. The reactor inlet temperature was periodically adjusted to maintain a 100 RON (research octane number) clear $C_5+$ product. Reforming conditions further included a liquid hourly space velocity of 2.0, a reactor outlet pressure of 300 psig., and a hydrogen/hydrocarbon mole ratio of about 2.5. The test results are tabulated below for each test period in terms of the liquid volume percent $C_5+$ yield, mole % hydrogen in the excess separator gas and reactor block temperature required to maintain a 100 RON product.

| Period No. | Reactor Temp. °C. | Recycle Gas. Mole % $H_2$ | $C_5+$ Yield, L.V. % |
| --- | --- | --- | --- |
| 1 | 507 | 77.8 | 73.2 |
| 2 | 511 | 77.3 | 73.6 |
| 3 | 515 | 76.2 | 72.6 |
| 4 | 517 | 76.9 | 73.0 |
| 5 | 518 | 76.8 | 72.8 |
| 6 | 519 | 77.3 | 72.9 |
| 7 | 520 | 77.6 | 72.9 |
| 8 | 522 | 77.1 | 72.6 |
| 9 | 523 | 76.8 | 72.6 |
| 10 | 524 | 75.7 | 72.1 |

We claim as our invention:

1. An alumina preparation method comprising:
   (a) admixing a finely divided alpha-alumina monohydrate with an aqueous ammonical solution having a pH of at least about 7.5 and forming a stable suspension;
   (b) commingling a metal salt of a strong acid with said suspension and converting said suspension to a extrudable paste or dough;
   (c) extruding said paste or dough; and
   (d) drying and thereafter calcining the extruded alumina product at a temperature of from about 450°–850° C.

2. The method of claim 1 further characterized with respect to step (a) in that said alumina is a water hydrolysis product of an aluminum alkoxide.

3. The method of claim 1 further characterized with respect to step (a) in that said alumina is a water hydrolysis product of an aluminum alkoxide produced by the Ziegler process.

4. The method of claim 1 further characterized with respect to step (a) in that said alkaline solution is an aqueous ammoniacal solution having a pH of from about 7.5 to about 8.5.

5. The method of claim 1 further characterized with respect to step (b) in that said metal salt of a strong acid is a nitrate.

6. The method of claim 1 further characterized with respect to step (b) in that said metal salt of a strong acid is aluminum nitrate.

7. The method of claim 1 further characterized with respect to step (b) in that said metal salt of a strong acid is aluminum nitrate employed in an amount to provide from about 2 to about 10 wt. % of the alumina in the final product.

8. The method of claim 1 further characterized with respect to step (b) in that said suspension comprises from about 30 to about 60 wt. % alumina.

9. The method of claim 1 further characterized with respect to step (d) in that said alumina product is calcined at a temperature of from about 550° to about 750° C. to provide a surface area of from about 165 to about 215 square meters per gram, and a pore volume of from about 0.3 to about 0.4 cc/g in the pore diameter range of from about 20 to about 80 Angstroms.

* * * * *